United States Patent [19]

Roberts et al.

[11] Patent Number: 4,805,609
[45] Date of Patent: Feb. 21, 1989

[54] PRESSURIZED VENTILATION SYSTEM FOR PATIENTS

[75] Inventors: Josephine A. Roberts, 7509 Ben Avon Rd., Bethesda, Md. 20817; Jephthae W. Burwell, Washington, D.C.

[73] Assignee: Josephine A. Roberts, Bethesda, Md.

[21] Appl. No.: 74,867

[22] Filed: Jul. 17, 1987

[51] Int. Cl.$^4$ .................. A61M 16/10; A61M 16/20
[52] U.S. Cl. ........................ 128/200.21; 128/202.27; 239/338; 239/352; 141/27
[58] Field of Search ............... 128/200.14, 200.19, 128/200.21, 202.27, 203.16; 604/4, 32, 248; 137/888; 261/78.2, DIG. 65; 239/338, 352; 141/25, 26, 27

[56] References Cited

U.S. PATENT DOCUMENTS

| | | | |
|---|---|---|---|
| 3,185,179 | 6/1965 | Harautuneian | 604/248 X |
| 3,232,292 | 2/1966 | Schaefer | 128/200.14 |
| 3,990,442 | 11/1976 | Patneau | 128/200.14 |
| 4,253,501 | 3/1981 | Ogle | 141/27 |
| 4,301,970 | 11/1981 | Craiglero | 239/338 |
| 4,366,105 | 12/1982 | Nowachi | 261/DIG. 65 X |

FOREIGN PATENT DOCUMENTS 58945  9/1936  Norway .................. 128/200.21

Primary Examiner—A. Michael Chambers
Assistant Examiner—John C. Fox
Attorney, Agent, or Firm—Raymond N. Baker

[57] ABSTRACT

A novel ventilating system (10) for human patients including nebulizing means (15A) for nebulizing a liquid medication into a supply (28A, 29A) of humidified breathable gas under pressure. The nebulizing means (15A) comprises a nebulizing module having a cap portion (25) to which is attached a vial-like nebulizing chamber (54A). In order to maintain the hermetic integrity of the system (10) a two-position, flow control valve assembly (64) is operatively connected to and in selective flow communication with, a lower region of the vial-like, liquid-retention nebulizing chamber (54A). The valve assembly (64) is configured so that it can be manually actuated between a first position precluding access to chamber (54A) or a second position for drainage of liquid (59A) from within the nebulizer chamber (54A) or addition of liquid to such chamber while maintaining system sealing and pressure. A liquid handling means such as a syringe (68) is used to control withdrawal or addition of liquid.

6 Claims, 2 Drawing Sheets

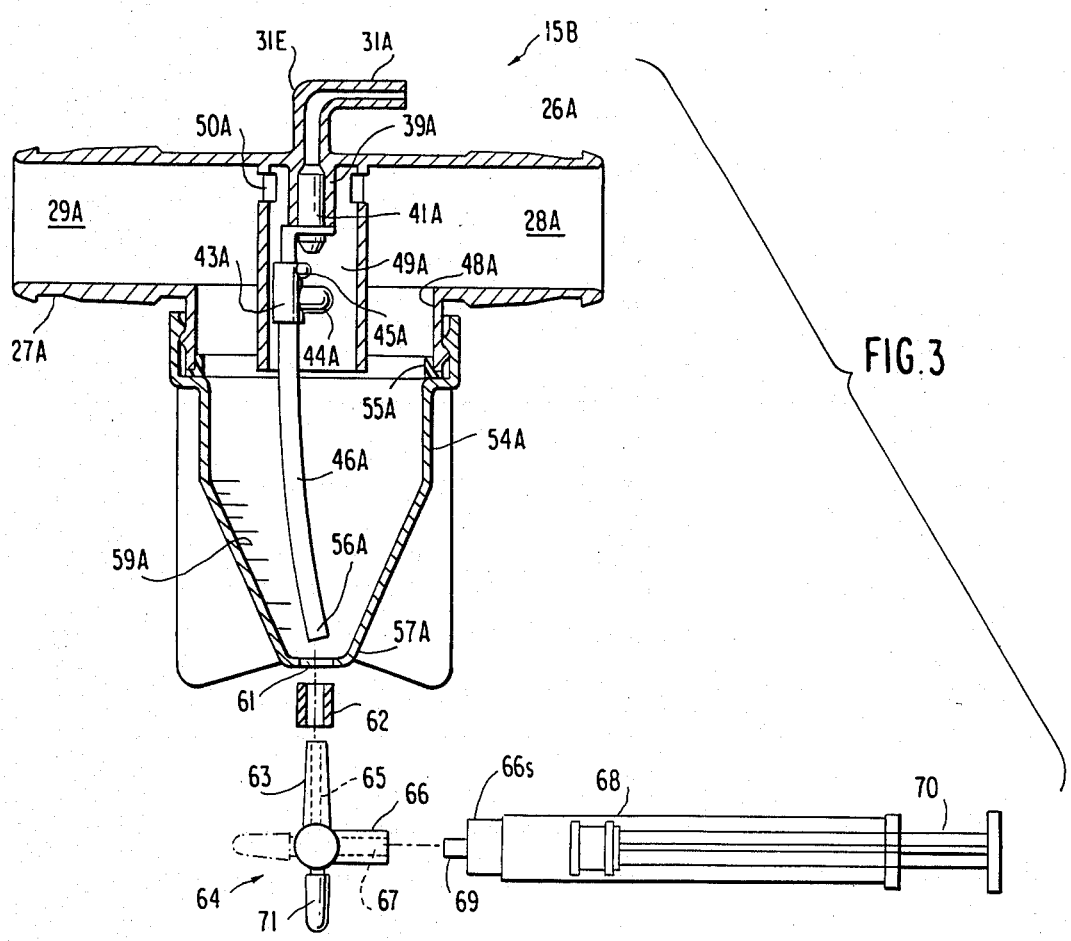
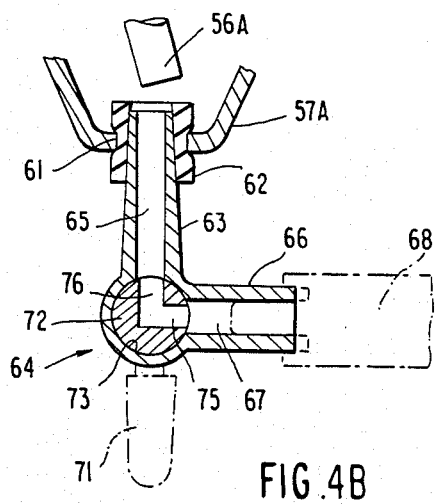
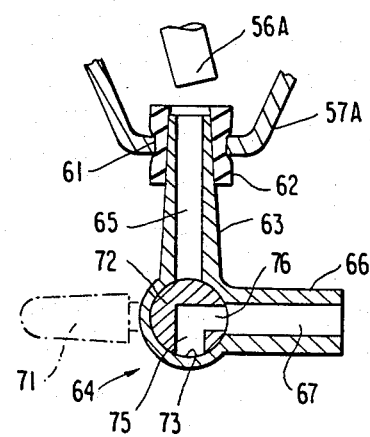

PRESSURIZED VENTILATION SYSTEM FOR PATIENTS

The present invention provides a closed ventilator system with nebulizer apparatus and methods for safe removal of contaminated moisture from, and addition of medication to, the system via such nebulizer means of such apparatus.

Patients in modern intensive care units who require continuous mechanical ventilation with a positive-pressure ventilator are critically ill. They are dependent upon a machine to sustain life, and disconnection from the machine or a leak in the pressurized system can be life threatening.

Modern mechanical ventilation of a patient is complex and the apparatus must be closely monitored by therapists and nurses. Oxygen-enriched gas is delivered under positive pressure from the ventilator to the patient by way of the ventilator circuit, including a bacteria filter, a humidifier, a nebulizer (atomizer device) and an exhalation valve, which are connected together by lengths of flexible, plastic tubing.

In the commonly-used positive-pressure ventilators, there is an ever present risk of introducing infectious agents to an already debilitated patient. Also, there is a risk of loss of the requisite oxygen percentage level and positive pressure, sometimes due to the structural leaks in the apparatus, but, more realistically, to the previous need to periodically open the system for medical purposes and the potential for creating leaks into the system such need represented.

One element that is especially vulnerable to these operating hazards is the nebulizer which is included in the ventilator system for the purpose of atomizing and delivering medication to the air passages and lungs. Prescribed medications are often ordered by the physician to be atomized at regular intervals, along with the inspired gas, to help, for example, liquify secretions that accumulate in the patient's airways and to treat bronchospasm.

Previously, in order to give these nebulizer treatments, the therapist or nurse was required to completely break the airtight seal of the ventilator circuit by unscrewing the cup-like element of the nebulizer. Any moisture that had accumulated in the cup was then emptied out, a medication placed in the cup and the cup screwed back in place. Such a procedure creates the following problems:

1. The nebulizer has to be emptied of accumulated moisture and the medication added rather hurriedly in order to minimize the disconnect time. This may result in spillage or only partial removal of the moisture, and spillage or only partial insertion of the medication.

2. In a critically ill patient, the total loss of pressure and oxygen enrichment during this procedure, can cause an alteration in the cardiopulmonary dynamics, hypoxemia, bradycardia, cardiac arrhythmias and destabilization of the patient.

3. Some patients are so unstable that there may be dramatic deterioration in their vital signs if the integrity of the ventilator circuit is broken only momentarily. This negates the possibility, with the existing system, of emptying accumulated moisture from the nebulizer cup, adding the medication and giving nebulizer treatments. See "*Complications of Mechanical Ventilation*", Moser, K. M., Respiratory Care, Vol. 20, No. 9, April 1975.

4. Every time the nebulizer cup is unscrewed, there is the potential for creating an ongoing leak in the system, if care is not taken when screwing the cup back on. The leak may be almost complete and the equivalent of an accidental disconnect, or it may be a partial leak that could go undetected for some time. The resulting deterioration in the arterial blood gas measurements of the patient could be life threatening.

5. Intensive care patients are debilitated with pronounced susceptibility to infection. Respiratory therapy equipment is always a potential source of infection to such patients due to the presence of warm humidified gas, water reservoirs and atomized particles of moisture. One of the greatest concerns in an intensive care unit (ICU) is cross-contamination of the patients by the therapists or nurses who go from patient to patient. When the nebulizer cup is unscrewed to add medication, it exposes the entire ventilator system circuit, and therefore the patient, to the possibility of introducing infection by cross-contamination.

6. In a highly infectious patient, who has, for example, AIDS, tuberculosis, or hepatitis, the sudden break in the highly pressurized ventilator system can cause contaminated moisture, which often contains blood to spray out in the face of the therapist or nurse, exposing them to the possibility of infection by the patient's organisms. See "*Contaminated Condensate in Mechanical Ventilator Circuits,*" by D. E. Craven et al. *Am. Rev. Respir. Dis.* 1984; 129; 625–628.

A modified ventilator, which is capable of safe draining of contaminated moisture, and also of risk-free administration of medications, would comprise a useful advance with inline nebulizers, especially if it can be economically devised and adapted to presently employed systems.

One prior art system for administering a nebulized substance is described in U.S. Pat. No. 3,874,379. The system includes a nebulizer module and an exhaust module. The nebulizer module consists of a vial to contain liquid and has a structure for producing an aerosol of liquid particles of the medication for entrainment in a stream of gas. It is typical of the current devices which are safer and improved by the present invention.

Another apparatus for administering a nebulized substance, as a closely controlled dose of an aerosol, is described in U.S. Pat. No. 4,624,251. In that apparatus, gas flow through the nebulizer need not be interrupted between substance administration, as is the case with earlier devices.

The invention provides a nebulizer means integrated with a ventilator system that precludes the several risks currently associated with nebulizer reservoir use and servicing. The invention provides an apparatus and a method of use which substantially reduces contaminant exposure to the patient as well as the therapist or nurse managing the continuous ventilation system. As a result of the invention the nebulizer component of the system can be serviced without breaking the pattern of preset positive pressure level, or the percent of oxygen enrichment provided for assisted breathing.

These and other contributions of the invention are considered in more detail by reference to the accompanying drawing, wherein:

FIG. 3 is an elevational sectional view, partly diagrammatic and enlarged, of the nebulizer means of the present invention spaced apart from the nebulizing means with which it cooperates and the ancillary syringe means;

FIG. 4A is a vertical sectional view diagrammatically detailing the chamber accessing and closure means of the present invention in a first, non-access position, and FIG. 4B is a vertical section and diagrammatic view of the present invention in use and while mateable with the syringe means for addition/withdrawal of fluid from the sealed chamber of the nebulizing means.

Figure 1:
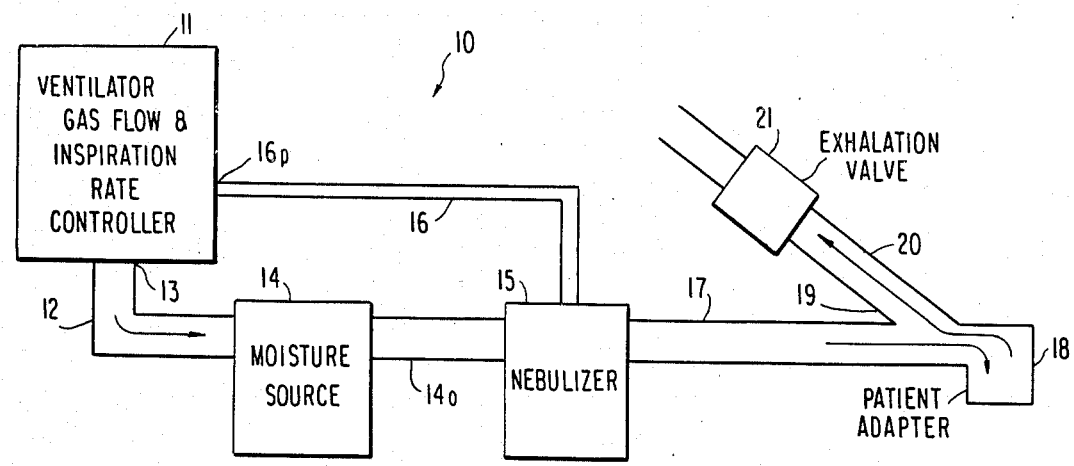
FIG. 1 is a schematic view of the major components for controlled ventilation and aerosolized substance introduction to a patient.

The patient ventilation system 10, shown schematically in FIG. 1, comprises a ventilator gas-flow and respiration-rate controller 11 which delivers air or oxygen-enriched gas. A main tubular conduit 12 connects with controller 11 and serves to pass a breathable gas through a moisture source (heated humidifier) 13. Humidification and warming is carried out continuously, to a preset degree, so as to compensate for the lack of humidity in the breathable gas as supplied and bring it to body temperature.

The humidified gas flows via conduit 14 directly to a manifold nebulizer 15, being operatively connected to the latter to pick up a normally liquid medication to be administered to the patient. A second conduit 16 flows from a port on the controller 11 to provide an ancillary supply of breathable gas which will permit aerosolization of the medication in a manner to be described. The thusly conditioned breathing gas departs the nebulizer means 15 via conduit 17 which itself terminates in a port on one of the two legs of a wye connector 18. To a second port, at the tail end of the wye connector, is attached a patient adaptor 19, which connects to an endotracheal tube (not seen) that passes via the nasal cavity, or mouth, to the patient's lungs. A third port on the second leg of the wye connector attaches to conduit 20 that ends in a one-way exhalation valve component 21.

When the flow of breathable gas is initiated from controller 11, during the inspiratory phase of ventilation, the exhalation valve is closed and the gas flows under positive pressure through the ventilator circuit to the patient via conduit 17, wye connector 18 and patient adaptor 19. At the termination of a pressurized breath to the patient, the exhalation valve opens and exhaled gas flows from the patient, through patient adaptor 19 down the exhalatory leg of the wye connector, through conduit 20 and past the open exhalation valve 21, which is well known in the art (U.S. Pat. No. 3,903,884), and is not part of this invention.

In FIG. 2, there is seen a state of the art nebulizer means, 15, comprising a stand-mountable head portion (not seen). Means 15 is operatively connected to gas supply conduits 14 and 16 (FIG. 1) by elements that will now be detailed.

The upper portion of the nebulizer module includes a cap portion 25. An inlet connection 26 extends laterally from one side of cap 25 and an outlet connection 27 extends laterally from the diametrically opposite side of cap 25. The central portion of cap 25 is predominantly hollow on its inside. Connectors 26 and 27 are aligned so as to have aligned through passageways 28 and 29, respectively. The connectors are open to the exterior of the cap and passages 28 and 29 communicate to provide a continuous through passageway in cap 25, as shown by the flow arrows in FIG. 2.

Extending upward from the central portion of cap 25 is a tubular projection 31 with a passageway 32 therethrough. A pressure reducer 33 can be attached on the open upper end of tubular extension 31 in frictional engagement therewith. A supply tube 34 can be attached directly to projection 31, or to projection 35 on reducer 33, as shown. Reducer 33 also includes a lateral tubular portion 36, which has a passageway 37 therethrough connecting with the interior of reducer 33. Lateral projection 36 is adapted to receive one-end of hose 38 thereon to provide fluid communication between the interior of hose 38 and the interior of cap 33.

In one embodiment, tube 38 connects with the top of nebulizer module 15A to the top of an exhaust module (not shown) via pressure reducer 33. This recognized function is described in U.S. Pat. No. 3,903,884, issued Sept. 9, 1975.

Projection 31 extends inwardly of cap 25 to form a nozzle housing 39. A nozzle 41 having a passageway therethrough and terminating in a restricted opening, is mounted in nozzle housing 39 and communicates with passageway 32 and thus with ancillary gas source 16.

A baffle assembly 43 is affixed to the nozzle housing 39 and includes a lateral baffle member 44 in alignment with the exit opening of nozzle 41 and an orifice 45 located intermediate baffle 44 and the opening of nozzle 41, which is substantially perpendicular to the flow of gas from nozzle 41.

The baffle assembly 43 receives an aspiration or suction tube 46 thereon with the passageway through tube 46 in communication with orifice 45. The nozzle, nozzle housing and baffle assembly are housed within a tubular chamber 49 defined by wall 47 extending downward from cap 25 and being concentric with the cylindrical skirt 48 or cap 25.

The chamber 49 is open at the bottom to permit exit of nebulized gas as shown by the arrows in FIG. 2, and has a pair of diametrically opposed openings 50 adjacent the top of the chamber. Each opening 50 is in alignment with one of the aligned connector portions of cap 25. The openings provide an inlet means for added gas from the main supply tube 12 to enter chamber 49 and pass therethrough to facilitate mixing and transfer of aerosol from the chamber 49 out through lateral connector 27, as seen in FIG. 1 (flow arrows).

The exterior surface of skirt 48 contains threads 52 which interengage with threads 53 on the outer upper rim of a vial 54. The top of vial 54 is open and the upper rim of the vial engages with a gasket 55 in cap 25 to provide a sealed engagement surface between vial and cap 25. Vial 54 may be transparent and is adapted to contain liquid to be introduced into the gas flow during operation. Suction tube 46 extends downwardly into vial 54 and has its bottom edge 56 located on a bulb-like reservoir 57 in the vial bottom. The dimensions of reservoir 57 are less than the dimensions of the remainder of the vial so that complete liquid usage is obtained. To prevent occlusion of open tip 56, a rib 58 is provided on the bottom of 57. A graduated scale 59 may be included on the transparent reservoir so that liquid medications may be monitored.

In operation, the main supply of gas is forced through tube 12, then through the major horizontal passageway 28 through cap 25 to exit from the open end of connector 27. A portion of that main gas flow is deflected through openings 50 into chamber 49. Gas from the ancillary source tube 16 passes through nozzle 41 and the venturi effect produced by flow through orifice 43 aspirates fluid through suction tube 46 and out through aperture 45. The liquid is then directed with the gas flow from nozzle 41 against baffle 44, where it is further broken up into small particles in the gas within chamber 49 producing an aerosol. The aerosol passes from the chamber out of the open bottom end thereof and into the main stream flow again for exit from cap 25 in the manner described above. In this manner, aerosol passes from the nebulizer module 15 through the flow system to the intubated patient via adapter 19. The operation within the nebulizer chamber is consistent with well known procedures for providing aerosol in a gaseous medium.

Figure 2:
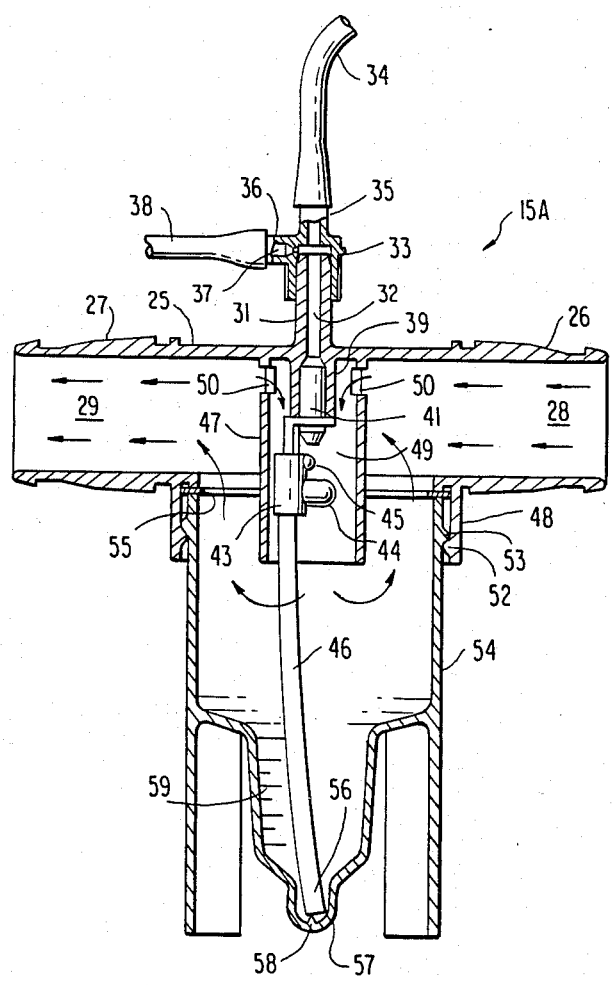
FIG. 2 is a fragmentary sectional view of a state-of-the-art nebulizing means (with its detachable cup in functioning position), as it would mounted adjacent to a conventional positive pressure ventilation system.

As earlier described, it is periodically required to interrupt the hermetical sealing of the prior art ventilation device of FIG. 2 for medical reasons, such as to access the vial receptacle 59, either to add the medication for aerosolization therein, or to cleanse that cup of settled-out condensed moisture. Interrupting the seal of the nebulizer means is done by manually unscrewing the lower component 54 and discarding the contents. Inevitably, the closed nature of the positive pressure system is thus violated. Supply gas can then escape freely to the ambient area, and a sudden backsurge occurring upon the system pressure release, can spew respired material out of the bottom of the header, so as to inadvertently contaminate the environs of the device with any accumulated pathogens. Complete reclosure of the nebulizer and restoration of the system integrity is vital.

Typical of the commercially available respiratory units which can be readily and effectively adapted to the present invention is the Dart manifold Nebulizer (two-component for cooperation with a Bennett MA-1 Ventilator).

FIG. 3 illustrates an enlarged view of a nebulizer means assembly 15A, modified to incorporate the present invention, and which is partially exploded to show the key components of the chamber access means. In this embodiment, however, the main gas ports are differently configured, with the breathable gas for the aerosolization entering via laterally disposed projection 31A, passing through an elbow 31E and flowing down nozzle passage 41A. This passage is likewise adapted to terminate with its restricted opening adjacent baffle assembly 43A which is affixed to nozzle housing 39A. Assembly 43A receives aspiration tube 46A. The nozzle, baffle assembly and suction tube all cooperate as described relative to the embodiment of FIG. 2, employing the dual gas sources for the venturi effect, and the liquid stored in vial bottom 57A, to aerosolize same, and flow it out of the nebulizing module to the patient connected via tubing (not seen) to outflow passage 29A.

The bottom of reservoir 57A has now been modified to provide a through port 61 at its lowermost point of the funnel portion. Normally disposed in port 61 is a hollow and resilient cylindrical sleeve 62, which is sized to accommodate the vertical nipple connector 63 of a closure assembly, generally 64. The nipple connector 63 has a first internal axial passage 65. The assembly also has an offset second nipple connector 66, with its internal axial passage 67, in communication with passage 65, thereby providing access between the environment external of the nebulizer means, and port 61.

Such nipple connector 66 is adapted to mate sealingly with the forward shoulder *66s* provided on a standard hypodermic syringe 68. The latter is provided at its distal part with the usual flanged end plunger 70.

As will be later detailed, syringe 68 will serve to either hermetically add medication to reservoir 57A, or to withdraw condensation collected in the cup, which undesirably would dilute the medication. When maintenance of the nebulizer cup is to be effected, the separation of the vial-like portion 54A from the nebulizer header can now be avoided. Note that there are two positions indicated for lever arm 71, which is operatively attached to an internal valve (not seen). One position maintains the sealing integrity of the nebulizer cup, and the other will vent the reservoir to the external environment. When a syringe is used for adding or drawing fluid, it is first properly preset, or charged, then it is sealingly mated to side nipple 66 on closure assembly 64, and will cooperate with the nebulizer in a manner now to be described.

Moving now to FIG. 4A, there is shown a schematic of the operating modes of the closure assembly 64. The cylindrical valve body 72 is manually rotatable in the circular chamber 73 provided in closure assembly 64. It is provided with a centrally located, elbow-shaped through passage 75. In the passive or sealed position, thumb lever 71 is adjusted so that potentially connecting axial passages 67 and 65 are isolated, since down leg 75 (and thus port 61 on vial 54A) does not communicate with the ambient space outside of the nebulizer. Thumb lever 71 is at 270° on a compass face. In this setting, neither the liquid substance in vial 57A, nor a loaded syringe 68 (FIG. 3) are in flowing communication with each other, and the operating integrity of the nebulizer means is preserved.

However, as indicated earlier, when access for servicing of the nebulizer cup is required, accessing is now made possible but without vitiating the ventilation system integrity. After mating the syringe tip 69 to side nipple 66, thumb lever 71 is moved downwardly through a 90° angle to 180° to provide communication between vial port 61 and external nipple passage 67 via central passages 75 and 76, as seen in FIG. 4B. In this posture, the mated syringe can now be activated, either to remove liquid from vial 57A (FIG. 3), or to inject fresh liquid medication into the cup.

Usually, one syringe is employed to drain condensed moisture; the valve is then closed, and the syringe is detached and emptied. Another syringe, loaded with medicine, is then mated, to nipple 66, and the valve assembly is actuated to permit introduction of the syringe contents into the nebulizer cup.

After the dual syringe function is achieved, the lever 71 is rotated back 90°, and thus returns the valve body 72 to the position of FIG. 4A, or a return to no flow communication. Thereafter, the syringe can be detached from side nipple 66, and the liquid nebulizing function is initiated, without having exposed the vial contents to ambient conditions, or having interrupted the level of positive pressure of the ventilator system.

The materials of construction for the nebulizer means components and the new components as well, are well known in the art. They are usually of a chemically-inert thermoplastic, such as polyolefins, polyvinylchlorides, or the ABS engineering plastics. Their selection and fabrication into the present structure described are incidental to the present invention, and well within the skill of the art.

The various liquid substances which may be delivered by the apparatus described include any of these which form aerosols when nebulized, such as the bronchodilator, isoetherine.

From the foregoing narrative, it will be apparent that the nebulization device of the present invention provides for an economical and disposable nebulizer system that permits customary nebulizer use and its facile maintenance, while having the features of reliable valving, proper patient and specialist shielding, and an ease of operation that clearly surpasses currently employed modes for nebulizer servicing.

While the invention has been described with reference to a particular embodiment, it will be appreciated that variations within the spirit and scope of the invention will occur to those skilled in the art. Thus, the present invention is not limited in scope to the preferred embodiments herein described.

We claim:

1. In a ventilatory support system for a human including means for providing a main supply of breathable gas under pressure, means for controlling the flow of such gas through a first conduit means and maintaining a desired pressure in such system, a moisture addition means operatively connected in said first conduit means, a nebulizer means hermetically sealed from the exterior of such system, operatively connected in the first conduit means, for generating an aerosol of a liquid substance in such flowing gas, exhalation means providing for intermittent exhalation while maintaining the pressure level in such system, and a secondary gas supply means for nebulizing gas connected to the nebulizer means, such nebulizer means comprising:

an inlet port, an outlet port and a nebulizing gas supply port, with said inlet port being operatively connected to the main supply of gas through the first conduit means, the outlet port connected to a second conduit means that communicates with the patient, and the nebulizing gas supply port being connected to such secondary gas supply means;

a vial-like member disposed within the nebulizer means and having a region for retaining a liquid substance to be atomized by the nebulizing gas; and a two-position valve means operatively connected to such region of the vial-like member, adapted to intermittently permit accessing the interior of said vial-like member to withdraw liquids accumulated therein or to add a liquid substance, such valve means including:

a valve body having a defined periphery adapted for movement within the valve means, such valve body defining:

a passage through the valve body intercepting such periphery of the valve body for providing communication between the interior of the vial-like member and the exterior of such system by being movable between a first position and a second position, with first position maintaining the hermetically sealed relationship and pressure level normally existing between the nebulizer vial and the exterior of such system drainage of any liquid substance standing in the liquid retaining region of the vial-like member by controllable liquid handling means and, alternatively, permitting introduction of a liquid substance into such region of the vial-like member for nebulizing; either liquid transfer step being carried out while maintaining the hermetically sealed relationship and pressure level of such system; and handle means for controlling the valve body and adapted to permit movement of the valve body between such first and second positions.

2. The system of claim 1 wherein the valve body passage is adapted to reside in either a flow-through position or a closed to-flow position when moved within the valve body.

3. The system of claim 1 wherein such valve means is provided with an outlet adapted to be operatively connected hermetically with such means for controlling liquid handling for entry or withdrawal of liquid from such region of the vial-like member when such valve body is in such second position.

4. The system of claim 3 wherein the connection means between such vial-like member and such means for controlling liquid handling is provided by first and second connectors disposed on the valve means having axial passages therein that communicate with such passage within said valve body when in such second position.

5. The system of claim 3 in which such means for controlling liquid handling includes a positive-pressure liquid injection means.

6. The system of claim 1 wherein the hermetical sealing is maintained during vial accessing by providing for sealing engagement between the valve means and such means for controlling liquid handling.

* * * * *

UNITED STATES PATENT AND TRADEMARK OFFICE
CERTIFICATE OF CORRECTION

PATENT NO. : 4,805,609
DATED : February 21, 1989
INVENTOR(S) : Josephine A. Roberts et al It is certified that error appears in the above-identified patent and that said Letters Patent is hereby corrected as shown below:

On the title page:
In the ABSTRACT, line 1, "ventilating" should be
   --ventilatory--.

Column 8, line 9, after "with" insert --the--;

line 12, after "system" insert --and, the second position adapted for permitting--;

line 26, insert a hyphen -- - -- after "closed".

Signed and Sealed this

Fourteenth Day of May, 1991

Attest:

HARRY F. MANBECK, JR.

Attesting Officer

Commissioner of Patents and Trademarks